United States Patent
Jackson (10) Patent No.: US 9,914,718 B2
(45) Date of Patent: Mar. 13, 2018

(54) ANHYDROUS CRYSTALLINE FORM OF S-EQUOL

(71) Applicant: Ausio Pharmaceuticals, LLC, Cincinnati, OH (US)

(72) Inventor: Richard L. Jackson, Cincinnati, OH (US)

(73) Assignee: AUSIO PHARMACEUTICALS, LLC, Cincinnati, OH (US)

( * ) Notice: Subject to any disclaimer, the term of this patent is extended or adjusted under 35 U.S.C. 154(b) by 198 days.

(21) Appl. No.: 14/883,617

(22) Filed: Oct. 14, 2015

(65) Prior Publication Data
US 2016/0102070 A1   Apr. 14, 2016

Related U.S. Application Data

(60) Provisional application No. 62/063,530, filed on Oct. 14, 2014.

(51) Int. Cl.
*A61K 31/35* (2006.01)
*C07D 311/04* (2006.01)

(52) U.S. Cl.
CPC .................. *C07D 311/04* (2013.01)

(58) Field of Classification Search
None
See application file for complete search history.

(56) References Cited

U.S. PATENT DOCUMENTS

| | | | |
|---|---|---|---|
| 7,396,855 B2 | 7/2008 | Setchell et al. | |
| 7,528,267 B2 * | 5/2009 | Setchell | C07D 311/04 549/399 |
| 7,960,432 B2 | 6/2011 | Setchell et al. | |
| 7,960,573 B2 | 6/2011 | Setchell et al. | |
| 8,048,913 B2 | 11/2011 | Setchell et al. | |
| 8,153,684 B2 | 4/2012 | Lephart et al. | |
| 8,263,790 B2 | 9/2012 | Setchell et al. | |
| 8,450,364 B2 | 5/2013 | Lephart et al. | |
| 8,580,846 B2 | 11/2013 | Lephart et al. | |
| 8,668,914 B2 | 3/2014 | Lephart et al. | |
| 8,716,497 B2 | 5/2014 | Setchell et al. | |
| 9,018,247 B2 | 4/2015 | Setchell et al. | |
| 9,173,866 B2 | 11/2015 | Setchell et al. | |
| 2005/0245492 A1 * | 11/2005 | Lephart | A61K 8/498 514/170 |
| 2006/0122262 A1 | 6/2006 | Lephart et al. | |
| 2011/0033564 A1 * | 2/2011 | Tominaga | A23L 1/3002 424/757 |
| 2012/0094336 A1 | 4/2012 | Steffan | |
| 2013/0136846 A1 | 5/2013 | Tominaga et al. | |
| 2015/0038570 A1 | 2/2015 | Setchell et al. | |

FOREIGN PATENT DOCUMENTS

WO   WO 2004009035 A2   1/2004

OTHER PUBLICATIONS

Chan et al. Phys. Chem. Chem. Phys., 2011, 13, 20361-20370.*
Chan et al. Angew. Chem. Int. Ed. 2011, 50, 2979 -2981.*
Jokela, T., "Systhesis of Reduced Metabolites of Isoflavonoids, and their Enantiomeric Forms," Academic Dissertation, Laboratory of Organic Chemistry, University of Helsinki, Finland, 28 pages (Nov. 26, 2011).
International Search Report and Written Opinion issued in International Application No. PCT/US2015/055467, 11 pages (dated Jan. 12, 2016).
Heemstra, J. et al., "Total Synthesis of (S)-Equol," Organic Letters, American Chemistry Society, 8:24, pp. 5441-5443 (2006).
Liang. G. et al., "X-Ray Single Crystal Analysis of (-)-(S)-Equol Isolated from Rat's Feces," Chemistry and Biodiversity, vol. 2, pp. 959-963 (2005).
Luk, Kin-Chun et al., "Isolation and Identification of "Diazepam-Like" Compounds from Bovine Urine," Journal of Natural Products, 46:6, pp. 852-861 (Nov.-Dec. 1983).
Morito, K. et al., "Interaction of Phytoestrogens with Estrogen Receptors α and β," Pharmaceutical Society of Japan, Biol. Pharm. Bull., 24:4, pp. 351-356 (2001).
Muthyala, R. et al., "Equol, A Natural Estrogenic Metabolite from Soy Isoflavones: Convenient Preparation and Resolution of R- and S-Equols and Their Differing Binding and Biological Activity Through Estrogen Receptors Alpha and Beta," Bioorganic & Medicinal Chemistry 12, pp. 1559-1567 (2004).
Setchell, K. et al., "The Clinical Importance of the Metabolite Equol—A Clue to the Effectiveness of Soy and Its Isoflavones," American Society for Nutritional Sciences, pp. 3577-3584 (Sep. 24, 2002).
Setchell, K. et al. S-Equol, A Potent Ligand for Estrogen Receptor β, is the Exclusive Enantiomeric Form of the Soy Isoflavone Metabolite Produced by Human Intestinal Bacteria Flora[1-4], Am. J. Clin. Nutr., vol. 81, pp. 1072-1079 (2005).

* cited by examiner

*Primary Examiner* — Jeffrey S Lundgren
*Assistant Examiner* — Michael Schmitt
(74) *Attorney, Agent, or Firm* — Rothwell, Figg, Ernst & Manbeck, p.c.

(57) ABSTRACT

An anhydrous crystalline form of S-equol has been discovered. Form I, the anhydrous crystalline form of S-equol has been isolated and characterized for the first time. As compared to other forms of S-equol, such as the known hydrate or other solvate forms, the anhydrous crystalline form of S-equol has improved properties.

19 Claims, 5 Drawing Sheets

FIG. 1

TABLE OF CHARACTERISTIC DIFFRACTION LINES FOR ANHYDROUS CRYSTALLINE POLYMORPH OF S-EQUOL, WITH RELATIVE INTENSITIES.

| POS. [°2Th.] | HEIGHT [cts] | FWHM [°2Th.] | D-SPACING [Å] | REL. INT. [%] |
|---|---|---|---|---|
| 11.4889 | 7252.75 | 0.0836 | 7.70233 | 54.87 |
| 13.2497 | 623.71 | 0.1004 | 6.68244 | 4.72 |
| 13.4639 | 275.69 | 0.0836 | 6.57657 | 2.09 |
| 16.4627 | 446.65 | 0.0669 | 5.38475 | 3.38 |
| 18.6400 | 7673.88 | 0.0836 | 4.76039 | 58.06 |
| 18.8941 | 7059.39 | 0.1004 | 4.69693 | 53.41 |
| 19.8495 | 12498.77 | 0.1171 | 4.47297 | 94.56 |
| 21.0873 | 13217.22 | 0.1338 | 4.21313 | 100.00 |
| 22.0035 | 8059.42 | 0.0836 | 4.03972 | 60.98 |
| 22.1819 | 7579.89 | 0.1004 | 4.00765 | 57.35 |
| 24.9712 | 1343.67 | 0.1338 | 3.56594 | 10.17 |
| 26.6871 | 3844.23 | 0.1506 | 3.34043 | 29.09 |
| 27.6666 | 363.47 | 0.0836 | 3.22436 | 2.75 |
| 29.2913 | 391.61 | 0.1171 | 3.04910 | 2.96 |
| 29.6821 | 257.17 | 0.1171 | 3.00985 | 1.95 |
| 30.0031 | 575.95 | 0.1506 | 2.97838 | 4.36 |
| 30.8292 | 2351.45 | 0.1338 | 2.90042 | 17.79 |
| 31.3110 | 1066.51 | 0.1004 | 2.85688 | 8.07 |
| 31.6839 | 104.90 | 0.1338 | 2.82410 | 0.79 |
| 32.7498 | 526.18 | 0.1338 | 2.73458 | 3.98 |
| 33.1193 | 152.36 | 0.1338 | 2.70492 | 1.15 |
| 34.0974 | 208.47 | 0.2040 | 2.62735 | 1.58 |
| 34.5236 | 136.91 | 0.1632 | 2.60234 | 1.04 |

ANHYDROUS CRYSTALLINE FORM OF S-EQUOL

CROSS REFERENCE TO RELATED APPLICATIONS

The present application claims benefit of U.S. Provisional Application No. 62/063,530, filed on Oct. 14, 2014, all of which is incorporated herein by reference in its entirety for all purposes.

FIELD OF THE INVENTION

This invention relates to an anhydrous crystalline form of S-equol (an active pharmaceutical ingredient), a method for the preparation of an anhydrous crystalline form of S-equol, and methods for the treatment of various diseases and conditions by administering an anhydrous crystalline form of S-equol to a subject in need thereof.

BACKGROUND OF THE INVENTION

Isoflavones and many derivatives thereof possess a wide range of important biological properties including estrogenic effects. Isoflavanoids found in soy, such as genistein and daidzein, have also attracted interest as dietary phytoestrogens that might be effective for the treatment of hormone-dependent conditions and diseases. In examining the impact of the estrogenic activity of soy isoflavones (commonly referred to as phytoestrogens), one needs to consider not only the isoflavones and their conjugates that are ingested, but also biologically active metabolites that might be generated in vivo. Daidzein can be converted to the corresponding chromane S-equol, a compound with greater estrogenic activity than its precursor. Setchell et al., *J. Nutrition*, 2002, 132(12): 3577-3584. This reductive metabolic conversion is the result of the action of equol-producing gut microflora found in a small proportion of the human population who are known as "equol producers."

Equol was first isolated from a pregnant mare's urine in 1932 and was subsequently identified in the plasma of red clover-consuming sheep. In 1982, equol was identified in human urine. Equol has a chiral center and therefore can exist in two enantiomeric forms. It has been recently established that S-equol is the exclusive enantiomer produced by intestinal bacterial flora in the metabolic reduction of isoflavones ingested by humans. Setchell et al., *American Journal of Clinical Nutrition*, 2005, 81:1072-1079.

The structure of S-equol is shown below.

S-equol, R-equol, non-racemic mixtures of S- and R-equol ("equol"); compositions of equol; processes for the preparation of equol; and methods of using equol are described in U.S. Pat. No. 8,716,497 (filed Sep. 10, 2012); U.S. Pat. No. 8,048,913 (filed Sep. 14, 2009); U.S. Pat. No. 7,960,432 (filed Jul. 3, 2008); U.S. Pat. No. 7,396,855 (filed Jul. 24, 2003); U.S. Pat. No. 8,263,790 (filed Jun. 1, 2011); U.S. Pat. No. 7,960,573 (filed May 4, 2009); U.S. Pat. No. 7,528,267 (filed Aug. 1, 2005); U.S. Pat. No. 8,668,914 (filed Jul. 31, 2009); U.S. Pat. No. 8,580,846 (filed Aug. 18, 2006); U.S. Pat. No. 8,450,364 (filed Apr. 9, 2012); and U.S. Pat. No. 8,153,684 (filed Oct. 2, 2009); each of which is incorporated by reference in its entirety.

Drugs utilized in the preparation of pharmaceutical formulations for commercial use must meet certain standards, including GMP (Good Manufacturing Practices) and ICH (International Conference on Harmonization) guidelines. Such standards include technical requirements that encompass a wide range of physical, chemical, and pharmaceutical parameters.

For example, a drug utilized for the preparation of pharmaceutical formulations should meet an acceptable purity. There are established guidelines that define the limits and qualification of impurities in new drug substances produced by chemical synthesis; that is, actual and potential impurities most likely to arise during the synthesis, purification, and storage of the new drug substance. Guidelines are instituted for the amount of allowed degradation products of the drug substance, or reaction products of the drug substance with an excipient and/or immediate container/closure system. In the guidelines, moisture specifications must be met.

Stability is also a parameter considered in creating pharmaceutical formulations. A stable drug product will ensure that the desired chemical integrity of drug substances is maintained during the shelf-life of the pharmaceutical formulation, which is the time frame over which a product can be relied upon to retain its quality characteristics when stored under expected or directed storage conditions. Different factors, such as light radiation, temperature, oxygen, humidity, and pH sensitivity in solutions, may influence stability and may determine shelf-life and storage conditions.

Bioavailability is also a parameter to consider in drug delivery design of pharmaceutically acceptable formulations. Bioavailability is concerned with the quantity and rate at which the intact form of a particular drug appears in the systemic circulation following administration of the drug. The bioavailability exhibited by a drug is thus of relevance in determining whether a therapeutically effective concentration is achieved at the site(s) of action of the drug.

Many pharmaceutical solids exhibit polymorphism, which is generally defined as the ability of a substance to exist as two or more crystalline phases (i.e., different arrangements and/or conformations of the molecules in a crystal lattice). Thus, polymorphs are different crystalline forms of the same substance in which the molecules have different arrangements and/or conformations of the molecules. As a result, the polymorphic solids have different physical properties, including those due to packing, and various thermodynamic, spectroscopic, interfacial, and mechanical properties.

Packing properties include the polymorph's molar volume and density, refractive index, thermal and electrical conductivity, and hygroscopicity. Thermodynamic properties include the polymorph's melting and sublimation temperatures, internal structural energy, enthalpy, heat capacity, entropy, free energy and chemical potential, thermodynamic activity, vapor pressure, and solubility. Spectroscopic properties include the polymorph's electronic transitions (ultraviolet-visible absorption spectra), vibrational transitions (infrared absorption spectra and Raman spectra), rotational transitions (far infrared or microwave absorption spectra), and nuclear spin transitions (nuclear magnetic resonance spectra). Kinetic properties include the polymorphs's dissolution rate, rates of solid state reactions, and stability.

Surface properties include the polymorph's surface free energy, interfacial tensions, and shape habit. Mechanical properties include the polymorph's hardness, tensile strength, compactibility (tableting), as well as handling, flow, and blending.

The various different chemical and physical properties of polymorphic forms can have a direct effect on the processing and/or manufacturing of the drug substance and the drug product. For example, the solid-state properties of the active ingredient will likely be critical to the manufacture of the drug product, particularly when it constitutes the bulk of the tablet mass in a drug product manufactured by direct compression. With respect to pharmaceutical processing, one of the most relevant factors for polymorphs is whether it can be consistently manufactured into a drug product that conforms to applicable in-process controls and release specifications.

Polymorphic forms of the drug substance can undergo phase conversion when exposed to a range of manufacturing processes, such as drying, milling, micronization, wet granulation, spray-drying, and compaction. Exposure to environmental conditions such as humidity and temperature can also induce polymorph conversion. The extent of conversion generally depends on the relative stability of the polymorphs, kinetic barriers to phase conversion, and applied stress. The most thermodynamically stable polymorphic form of a drug substance is often chosen during development based on the minimal potential for conversion to another polymorphic form and on its greater chemical stability. Therefore, it is important to find not only the most thermodynamically stable polymorphic form of a drug substance, but also the polymorphic form that is most amenable to a large-scale manufacturing process.

Crystallization and drying are two of the most difficult operations in a scale-up process, especially when the compound is polymorphic and can form a hydrate or solvates. In the case of hydrates, removal of water from the crystal lattice requires particularized conditions and is very much dependent on the temperature and humidity history of the sample. The mobility of water among various components in a formulation must always be considered. Water interacts with pharmaceutical solids at virtually all stages of manufacture. The amount of moisture absorbed by drugs and excipients effects the flow, compression characteristics, and hardness of granules and tablets. Thus, it is very important to establish that the desired form is produced and to minimize batch-to-batch variability.

In addition, it is desirable to regulate crystal polymorphism of a chemical substance, or an ingredient thereof, because differences in crystalline form may affect properties of the drug such as performance of the preparation, bioavailability, and stability. The difference in the physical properties of different solid state forms results from the orientation and intermolecular interactions of adjacent molecules or complexes in the bulk solid. Accordingly, polymorphs are distinct solids sharing the same molecular formula, while having distinct physical properties, which may be advantageous relative to other solid state forms of the same compound or complex.

Equol has been isolated in a crystal form in the literature. Liang et al., *X-Ray Single-Crystal Analysis of (−)-(S)-Equol Isolated from Rat's Feces*, Chemistry and Biodiversity 2005, 2, 959-963. However, as provided on page 960, the only crystal form disclosed is a hydrate of S-equol. Hydrate forms of crystalline materials are generally known to be less stable than anhydrous crystalline forms in certain conditions. Thus, there is a need in the art to provide a pure anhydrous crystalline form of S-equol having improved stability.

SUMMARY OF THE INVENTION

The following brief summary is not intended to include all features and aspects of the present invention, nor does it imply that the invention must include all features and aspects discussed in this summary.

The present invention generally relates to an anhydrous crystalline form of S-equol and pharmaceutical compositions thereof. Additionally, the invention relates to methods of making and using an anhydrous crystalline form of S-equol for the treatment of various diseases and disorders in a subject in need thereof. Preferably, the subject is a mammal.

The foregoing and other objects, features and advantages of the invention will be apparent from the more particular description of preferred embodiments of the invention, as illustrated in the accompanying examples and drawings. The drawings are not necessarily to scale, emphasis instead being placed upon illustrating the principles of the invention.

DETAILED DESCRIPTION OF THE INVENTION

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "polymorphism" refers to the capacity of a chemical structure to occur in different forms and is known to occur in many organic compounds, including drugs.

The term "crystalline" is defined as a form in which the position of the molecules relative to one another is organized according to a three-dimensional lattice structure.

As used herein the terms "anhydrous" and "anhydrate" are used interchangeably, and refer to a particular solid state form that is essentially free of water. Likewise, the terms "hydrous" and "hydrate" are used interchangeably and refer to particular solid-state forms having water molecules incorporated into the three-dimensional lattice structure.

One embodiment of the invention is a composition of an anhydrous crystalline form of S-equol. Such a composition comprises an anhydrous crystalline polymorph of S-equol, or in an alternative embodiment, anhydrous crystalline Form I of S-equol, and one or more acceptable adjuvants, carriers, and/or excipients. The composition may be used in making commercial and institutional products. The composition, or a product made therefrom, can be formulated for, or delivered by all the different routes of administration known in the art. For example, a composition comprising an anhydrate crystalline form of S-equol can be formulated for oral, rectal, or cutaneous administration. Preferably, the composition is administered orally. The composition can be administered in the form of tablets, capsules, or powder. Additionally, buccal mucosal products and orally disintegrating tablets are included. The composition can be administered via a transdermal patch or other topical device. The most suitable route in any given case will depend on the nature and severity of the condition being treated and the health of the patient.

The product includes a pharmaceutical, a dietary supplement, a food product, or an over-the-counter medicament containing an anhydrous crystalline form of S-equol. An orally-administered medicament can comprise at least 1 mg, and up to 200 mg, per dose of an anhydrous crystalline form of S-equol. For example, a dose of 5, 10, 20, 50, 100, 150, or 200 mg may be used.

A composition or preparation of an anhydrous crystalline form of S-equol can be administered to subjects to treat, prevent, or reduce the predisposition to diseases and/or conditions related thereto. Such a composition or preparation can also comprise one or more pharmaceutically acceptable adjuvants, carriers, and/or excipients. Adjuvants, carriers, and/or excipients are well known in the art, and are described, for example, in the Handbook of Pharmaceutical Excipients, second edition, American Pharmaceutical Association, 1994, which is incorporated by reference in its entirety.

Another embodiment of the invention is a method for the preparation of an anhydrous crystalline polymorph of S-equol. In previous reports, S-equol was prepared from (S)-bis-MOM-equol using a 10 wt % solution of HCl in methanol. See, e.g., Example 6 in U.S. Pat. Nos. 8,716,497; 8,263,790; 7,960,573; and 7,528,267. According to that procedure, the reaction mixture was allowed to slowly warm from 0° C. to room temperature. After six hours at room temperature, the reaction was stopped, and the product was isolated using standard laboratory techniques. The procedure resulted in a high yield of S-equol having a chemical purity of 96.69% and a water content of 7%; however, the procedure was not optimized for large-scale (i.e., kilogram) production.

It was found that a new method of preparing S-equol allowed for its purification and isolation in anhydrous crystalline form. By reacting (S)-bis-Piv-protected-equol (Piv=t-butylacyl or —C(O)-tBu) with KOH in methanol, S-equol can be obtained having a chemical purity of 99.5% and a water content of less than 4%. Moreover, the process is amenable to large-scale synthesis of anhydrous crystalline S-equol.

Another embodiment of the invention is a method of delivering an anhydrous crystalline form of S-equol to a subject, patient, or mammal. The active agent can be administered in an amount sufficient to produce a transient level of S-equol in the blood plasma of the mammal of at least 5 nanograms per milliliter (ng/mL), more typically at least 10 ng/mL or greater, or transient levels of S-equol in urine of greater than 1000 nmol/L.

Compositions of an anhydrous crystalline form of S-equol can be used to treat a variety of hormone-dependent diseases and conditions associated therewith.

The anti-androgenic activity of equol can affect a number of tissues throughout the body. In particular, the methods include the treatment and prevention of: (A) growth of the prostate gland with aging, benign prostatic hyperplasia (BPH) and prostate cancer; (B) female- and male-pattern baldness, (C) facial and body hair growth (hirsutism), skin health (acne, anti-aging and anti-photo aging), skin integrity (collagen and elastin robustness); (D) body weight gain (and loss), reduction in adipose tissue deposition and metabolism of lipids, as well as general regulatory behaviors and effects, such as food and water intake, blood pressure changes, thyroid, glucose, leptin, insulin and the influence on the immune system; and (E) Alzheimer's disease and emotional, mental health issues, such as mood, depression, anxiety, and learning and memory.

Yet another embodiment of the invention relates to the use of an anhydrous crystalline form of S-equol for the prevention, treatment, or alleviation of a disease or disorder in a subject, which disease or disorder is treatable with equol. Such diseases or disorders may include one or more of the following: (1) lipid disorders such as high cholesterol (hypercholesterolemia), lipidemia, lipemia and dyslipidemia (disturbances in lipids); (2) osteopenia and osteoporosis; (3) acute and chronic ovarian estrogen deficiency states, including vasomotor disturbances and night sweats, commonly referred to as "hot flushes" or "hot flashes," and hot flushes accompanying antiestrogen therapy used in the treatment of breast cancer; (4) cardiovascular disease and liver disease; (5) an androgen-related condition and/or an estrogen-related condition in a mammal; (6) age-related androgen/estrogen hormonal imbalance; (7) physiological and pathophysiological conditions in a mammal; (8) diseases and conditions related to facial and body hair; (9) diseases and conditions related to the secretion of sebum (oil); (10) acne or other skin disruptions (scratches, popping pimples or minor cuts, etc.); (11) diseases and conditions related to skin effects, skin quality and integrity, skin aging, skin photoaging, and skin pigmentation and lightening; (12) diseases and conditions related to improved prostate health, including benign prostatic hyperplasia (BPH), and prostate cancer; (13) breast cancer; (14) diseases and conditions related to brain function and mental health, including brain disorders, dementia of the Alzheimer type, as well as other reduced or impaired cognitive functions associated with advancing age and with short- and long-term memory loss; or (15) a neuropsychiatric or neurodegenerative disease or disorder such as, depression, anxiety, bipolar disorder, obsessive-compulsive disorder, hyperactive disorder, weight gain, obesity, Alzheimer's disease, Parkinson's disease, or a peri- or postmenopausal symptom.

EXAMPLES

Example 1

S-equol was prepared by treating bis-pivaloyl-S-equol with aqueous KOH in methanol at 0° C., and then allowing the solution to warm to room temperature. After about 1.5 hours, the reaction was cooled and ice was added to the solution, which was followed by the addition of acetic acid. The solution was then concentrated and the resulting suspension was washed with water to remove MeOH. After stirring for about 20 hours, the resulting solid was washed with water and hexanes and the damp solid was dried under vacuum to give an off-white solid. Next, the solid was suspended in heptane and ethyl acetate, and after about 20 hours, the solid was collected by filtration, washed with heptane/ethyl acetate, then heptane, and isolated under vacuum to provide S-equol.

Example 2

Anhydrous crystalline S-equol was obtained using an evaporation crystallization method. A 50 mg of sample of S-equol was weighed in a glass tube. Depending on the solubility, 1, 2, or 3 ml of solvent was added. The solubility was tested step-wise, so that after the first addition of 1 ml of solvent, the suspension was stirred for at least 1 h. If the solid had not fully dissolved, a further 1 ml of solvent was added (50 g/l) and the stirring was continued again for an hour. This step was repeated to give a maximum of 3 ml (16.7 g/l) of solvent per experiment, giving then either clear solutions or suspensions for the evaporation step. The glass tubes were placed under nitrogen flow and solvents were left to evaporate. This took, depending of the solvent and applied temperature, from a few hours to several days. After evaporation of the solvents, the achieved solids were analyzed by XRPD.

Example 3

Anhydrous crystalline S-equol was obtained using a cooling crystallization method. In each experiment a saturated or close-to-saturated solution was prepared at the starting temperature of the experiment. In crash cooling experiments, the clear solution was put into an ice bath and left to stand for two hours. The sample was filtered and analyzed with XRPD. In slow cooling experiments, the saturated solutions were cooled down to 0° C. with a cooling rate of 5 K/min, after which the sample stood for two hours at end temperature before filtration and XRPD analysis.

Example 4

Anhydrous crystalline S-equol was obtained using a precipitation method. In each experiment, the precipitation crystallizations were carried out by using either water or n-heptane as the antisolvent and precipitation agent. The solvents and experimental parameters used, as well as results, are summarized in Table 1.

TABLE 1

Summary of precipitation crystallizations on 200 mg of S-equol.

| Solvent, volume (mL) | Anti-solvent, volume (mL) | Result |
|---|---|---|
| 1,4-dioxane, 5 | Water, 20 | Form II Hydrate |
| DMSO, 5 | Water, 15 | DMSO solvate |
| acetic acid, 6 | Water, 15 | Form II Hydrate |
| IPA, 5 | Water, 20 | Form II Hydrate |
| nitromethane, 15 | Water, 15 | oiled out |
| IPA, 5 | n-heptane, 35 | Form II Hydrate |
| 1,4-dioxane, 5 | n-heptane, 10 | oiled out |
| acetic acid, 5 | n-heptane, 30 | Form I |
| ethyl acetate, 5 | n-heptane, 80 | Form II Hydrate |
| MEK, 5 | n-heptane, 25 | Form II Hydrate |

The hydrate (Form II) resulted from most of the precipitation crystallizations. For example, three of the precipitation experiments using n-heptane as the anti-solvent gave the hydrate form. The precipitation from DMSO resulted, however, as a new solvated crystal form. This shows that the hydrate forms very willingly, and why it is the only form disclosed in the prior art.

Figure 2:
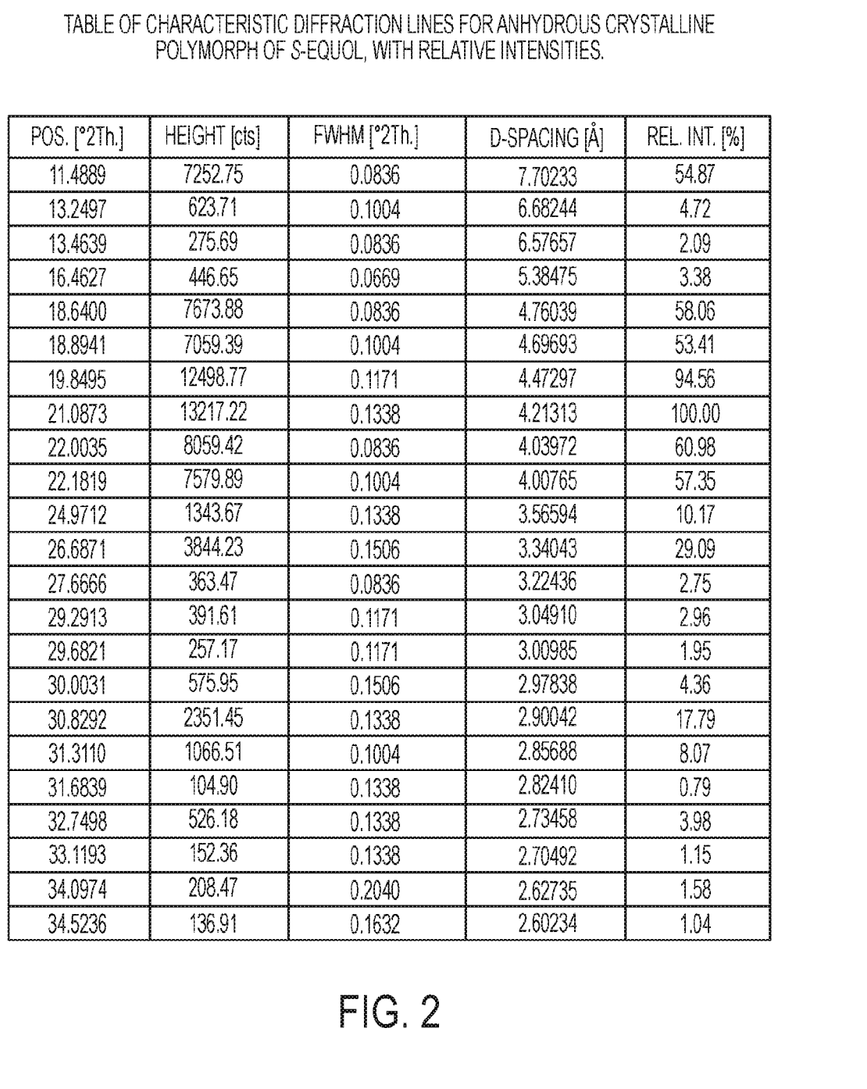
FIG. 2 depicts a table of characteristic diffraction lines for anhydrous crystalline S-equol.
Figure 3:
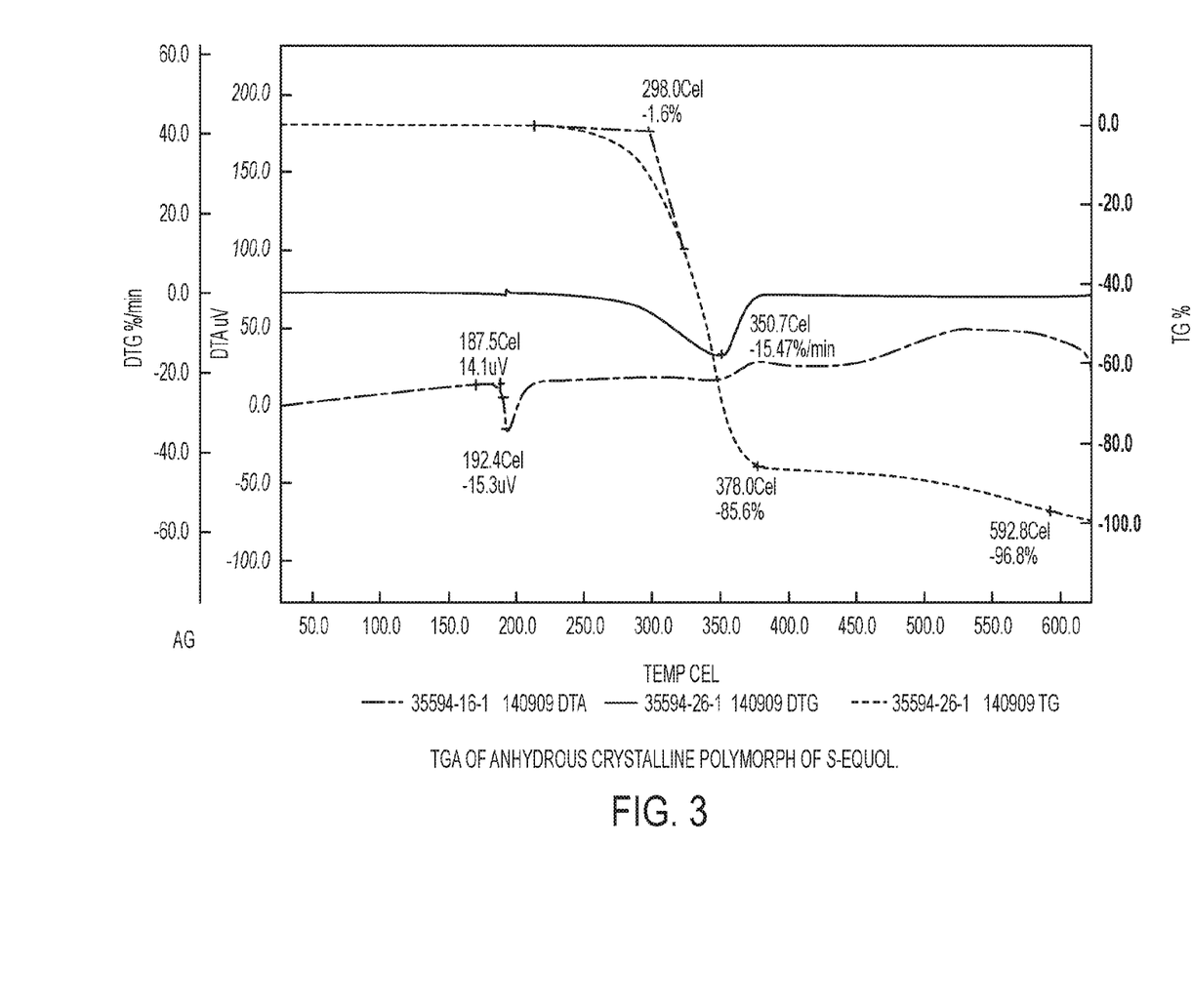
FIG. 3 depicts a Thermal Gravimetric Analysis (TGA) for anhydrous crystalline S-equol.
Figure 4:
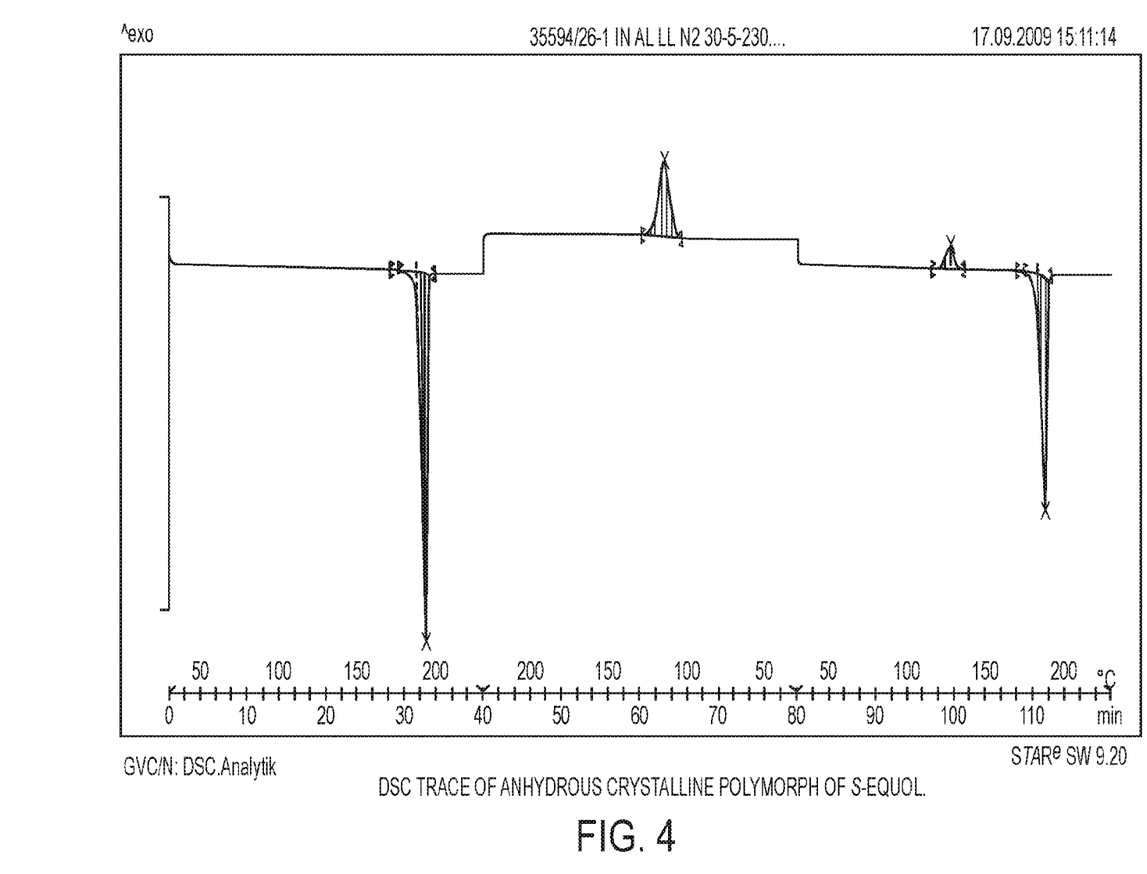
FIG. 4 depicts a Differential Scanning calorimetry (DSC) curve for anhydrous crystalline S-equol.

X-ray powder diffraction: The X-ray powder diffractograms were recorded using a Panalytical X'Pert Pro diffractometer in reflection geometry in the range from 2θ=3°-35° C. with increments of 0.0167° C. using Cu radiation at 20° C. The recorded 2θ values were used to calculate the stated interplanar spacings d. The intensity of the peaks (y-axis: linear intensity counts) is plotted versus the 2θ angle (x-axis in degrees 2θ). The characteristic diffraction results are provided in FIG. 2 and summarized in Table 2.

TABLE 2

Characteristic diffraction lines for Form I of anhydrous crystalline S-equol with relative intensities.

| Position (degrees 2 theta) | Relative intensity (%) |
|---|---|
| 21.09 | 100 |
| 19.85 | 94.56 |
| 22.00 | 60.98 |
| 18.64 | 58.06 |
| 21.18 | 57.35 |
| 11.49 | 54.87 |
| 18.89 | 53.41 |
| 26.69 | 29.09 |

Differential Scanning calorimetry: DSC was performed on a Mettler Toledo DSC 822e module. Crystals coming from solution crystallization and taken from a mother liquor were dried gently on a filter paper and laced in a crimped but vented aluminum sample pans for the DSC experiments. The sample size in each case was 5 to 10 mg. The starting temperature was in each measurement 30° C., but the end temperature varied from case to case, but was typically below 200° C. The heating rate was 1, 2, 5 or 10 K/min. The samples were purged with a stream of nitrogen flowing at 150 mL/min for the DSC experiment.

Thermal Gravitational Analysis: TGA/DTA analysis was carried out with a Mettler Toledo TGA/SDTA 851 using $Al_2O_3$ as reference. The samples (8-30 mg) were placed platinum sample pans for a measurement under nitrogen flow with a temperature program from 30 to 605° C. at 10° C./K.

Hot stage microscopy was carried out on a Mettler FP82HT hot stage connected to a Mettler FP90 central processor and Olympus BH-2 Microscope. The primary heating rate used was 5° C./min from 30° C. to melting temperature of the sample with a light microscope.

Figure 5:
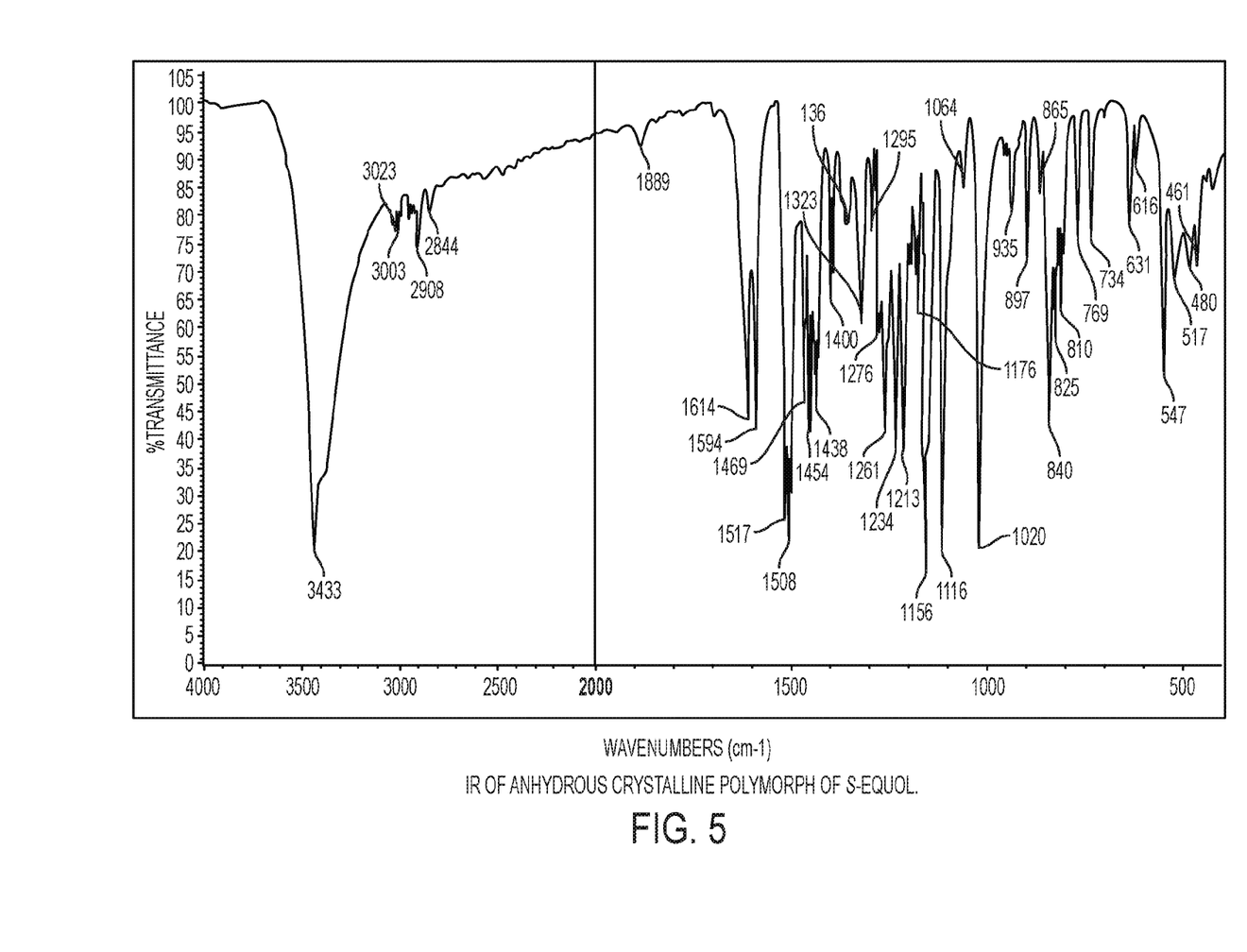
FIG. 5 depicts an Infrared (IR) Spectroscopy spectrum for anhydrous crystalline S-equol.

Infrared Spectroscopy: An IR analysis was carried out with and FTIR-Spektrometer Nicolet 6700. An IR spectrum for anhydrous crystalline S-equol is provided in FIG. 5 and summarized with the following characteristic wavenumbers ($cm^{-1}$): 3433, 3023, 3003, 2908, 2844, 1889, 1614, 1594, 1517, 1508, 1469, 1454, 1438, 1400, 1361, 1323, 1295, 1276, 1261, 1234, 1213, 1176, 1156, 1116, 1064, 1020, 935, 897, 865, 840, 825, 810, 769, 734, 631, 616, 547, 517, 480, and 461.

Stability testing: To access its ability to maintain a desired chemical integrity, the stability of anhydrous crystalline polymorph of S-equol was evaluated for a period representative of the shelf-life of a pharmaceutical formulation. Anhydrous crystalline polymorph of S-equol was maintained at room temperature storage conditions, and evaluated for purity and water content. The testing results are provided in Table 3.

TABLE 3

Long-term stability testing of anhydrous crystalline S-equol.

| Test Date | Appearance | Purity (HPLC area %) | Water Content (g/100 g) |
|---|---|---|---|
| 0 days | white to brown powder or crystal | 100% | <0.1 |
| 626 days | white to brown powder or crystal | 100% | 0.05 |
| 867 days | white to brown powder or crystal | 100% | 0.05 |

The examples are provided to aid in the understanding of the present invention, the true scope of which is set forth in the appended claims. It is understood that modifications can be made in the procedures set forth without departing from the spirit of the invention.

While this invention has been particularly shown and described with references to preferred embodiments thereof, it will be understood by those skilled in the art that various changes in form and details may be made therein without departing from the scope of the invention encompassed by the appended claims.

The invention claimed is:

1. An anhydrous crystalline polymorph of S-equol, represented by the structure wherein said polymorph is characterized by an X-ray powder diffraction pattern having characteristic peaks expressed in degrees 2θ at about 11.49, 18.64, 18.89, 19.85, 21.09, 22.00, and 26.69.

Figure 1:
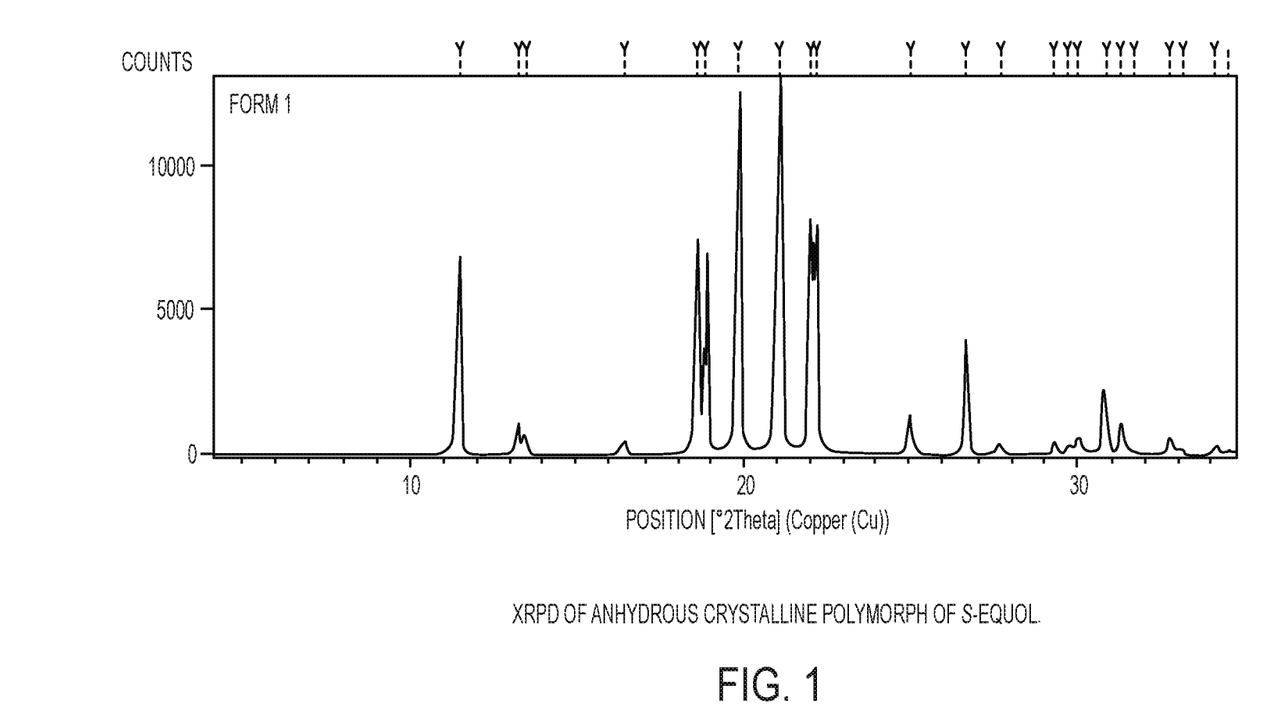
FIG. 1 depicts an X-ray powder diffraction pattern (XRPD) of anhydrous crystalline S-equol.

2. The anhydrous crystalline polymorph of S-equol of claim 1, characterized by an X-ray powder diffraction pattern that is substantially in accordance with FIG. 1.

3. The crystalline polymorph of S-equol of claim 1 having a moisture content of less than 4%.

4. The crystalline polymorph of S-equol of claim 3 which is 95% pure.

5. The crystalline polymorph of S-equol of claim 4 which is 99% pure.

6. A pharmaceutical composition comprising the anhydrous crystalline polymorph of S-equol of claim 1 and at least one pharmaceutically acceptable excipient.

7. A pharmaceutical composition comprising the crystalline polymorph of S-equol of claim 3 and at least one pharmaceutically acceptable excipient.

8. A crystalline polymorph of S-equol prepared by a process comprising reacting bis-pivaloyl-S-equol with a base, optionally in the presence of one or more solvent(s).

9. The crystalline polymorph of S-equol according to claim 8, wherein the base is KOH.

10. The crystalline polymorph of S-equol according to claim 8, wherein the one or more solvent(s) includes methanol.

11. The crystalline polymorph of S-equol of claim 8, further comprising crystallizing S-equol with acetic acid and heptane.

12. A method of mediating androgen hormone action in a subject in need thereof, comprising administering to the subject an effective amount of the anhydrous crystalline S-equol of claim 1.

13. The method of claim 12, wherein the hormone is leptin or thyroid (T3).

14. A method for treating a disease or condition in a mammal, comprising administering to the mammal the anhydrous crystalline S-equol of claim 1.

15. The method of claim 14, wherein the disease or condition is aging of skin or hair, weight gain or obesity, a neuropsychiatric disease or disorder, benign prostatic hyperplasia, prostate cancer, breast cancer, osteoporosis, hot flashes, and night sweats.

16. A method of mediating androgen hormone action in a subject in need thereof, comprising administering to the subject an effective amount of the crystalline polymorph of S-equol as defined in claim 3 or claim 8.

17. The method of claim 16, wherein the hormone is leptin or thyroid (T3).

18. A method for treating a disease or condition in a mammal comprising administering to the mammal the anhydrous crystalline S-equol of claim 3 or claim 8.

19. The method of claim 18, wherein the disease or condition is aging of skin or hair, weight gain or obesity, a neuropsychiatric disease or disorder, benign prostatic hyperplasia, prostate cancer, breast cancer, osteoporosis, hot flashes, and night sweats.

* * * * *